United States Patent

House et al.

[11] Patent Number: 5,212,196
[45] Date of Patent: May 18, 1993

[54] CONTROL OF POST-SURGICAL INTRAOCULAR PRESSURE USING CLONIDINE DERIVATIVES

[75] Inventors: Betty R. House, Euless; Joseph M. DeFaller, Bedford; Billie M. York, Fort Worth, all of Tex.

[73] Assignee: Alcon Laboratories, Inc., Fort Worth, Tex.

[21] Appl. No.: 918,874

[22] Filed: Jul. 24, 1992

Related U.S. Application Data

[63] Continuation of Ser. No. 615,950, Nov. 20, 1990, abandoned, which is a continuation of Ser. No. 311,789, Feb. 16, 1989, abandoned, which is a continuation of Ser. No. 921,175, Oct. 21, 1986, abandoned.

[51] Int. Cl.$^5$ ............................................ A62K 31/415
[52] U.S. Cl. ...................................... 514/392; 514/913
[58] Field of Search .............................. 514/392, 912

[56] References Cited

U.S. PATENT DOCUMENTS

| | | | |
|---|---|---|---|
| 3,202,660 | 8/1965 | Zeile et al. | 260/254 |
| 3,468,887 | 9/1969 | Stahle et al. | 260/253 |
| 4,461,904 | 7/1984 | York, Jr. | 548/315 |
| 4,515,800 | 5/1985 | Cavero et al. | 514/392 |
| 4,517,199 | 5/1985 | York, Jr. | 514/392 |
| 4,587,257 | 5/1986 | DeSantis et al. | 514/392 |

OTHER PUBLICATIONS

Ocular Therapeutics & Pharmacology, 6 ed, 1981, p. 88.
Rouot et al., "Clonidine and Related Analogues, Quantitative Correlations," *J. Med. Chem.*, 19(8):1049-1054 (1976).
Robin, A. L., "Intraocular Pressure Elevation Following Anterior Segment Laser Surgery", *Ophthalmic Laser Therapy*, 1(2):101-106 (1986).
Thomas et al., "Argon Laser Trabeculoplasty in the Presurgical Glaucoma Patient", *Ophthalmology*, 89:187-197 (1982).
Hoskins, Jr. et al., "Complications of Laser Trabeculoplasty", *Ophthalmology*, 90:796-799 (1983).
Weinreb et al., "Immediate Intraocular Pressure Response to Argon Laser Trabeculoplasty", *Am. J. Ophth.*, 95(3):279-286 (1983).
Krupin et al., "Intraocular Pressure the Day of Argon Laser Trabeculoplasty in Primary Open-angle Glaucoma", *Opthalmology*, 91:361-365 (1984).
Henry et al., "Increased Intraocular Pressure Following Neodymium-YAG Laser Iridectomy", *Arch. Opthal.*, 104:178 (1986).
Hodapp et al., "The Effect of Topical Clonidine on Intraocular Pressure", *Arch. Ophthal.*, 99:1208-1211 (1981).
Ofner et al., "Pilocarpine and the Increase in Intraocular Pressure After Trabeculoplasty", *Am. J. of Opth.*, 97(5):647-649 (1984).
Robin, A. L., "The Role of Apraclonidine Hydrochloride in Laser Therapy for Glaucoma", *Tr. Am. Ophthal.*, LXXXVII:729-761 (1989).

Primary Examiner—Fredrick E. Waddell
Assistant Examiner—Zohreh A. Fay
Attorney, Agent, or Firm—Julie J. L. Cheng; Gregg C. Brown; James A. Arno

[57] ABSTRACT

A method of controlling intraocular pressure by non-chronic, topical administration of a clonidine derivative immediately prior and post trauma to the affected eye.

22 Claims, No Drawings

CONTROL OF POST-SURGICAL INTRAOCULAR PRESSURE USING CLONIDINE DERIVATIVES

This application is a continuation of application Ser. No. 07/615,950, filed Sep. 20, 1990, now abandoned which is a continuation of application Ser. No. 07/311,789 filed Feb. 16, 1989, now abandoned which is a continuation of application Ser. No. 06/921,175 filed Oct. 21, 1986, now abandoned.

BACKGROUND OF THE INVENTION

1. Field of the Invention

This invention relates to the use of certain clonidine derivatives to control intraocular pressure, such as the pressure rise which occurs following ophthalmic surgery, non-invasive laser surgery, or other induced or accidental trauma to the eye.

2. Discussion of Related Art

This invention relates to the nonchronic actual and prophylactic control of increased intraocular pressure that frequently occurs as a result of eye surgery, non-invasive laser surgery, or any other form of intentional or accidental trauma to the eye. In particular, this invention relates to achieving such control through the use of certain clonidine derivatives applied topically to the eye immediately before and for a short period after the ocular trauma.

The class of so called clonidines or substituted phenyliminoimidazolines useful in the present method are disclosed in U.S. Pat. Nos. 4,461,904; 4,517,199; 4,515,800; 4,587,257; and 4,646,007; all of which are incorporated herein by reference to the extent that they individually and collectively define generically and name specifically such clonidine-like compounds or such substituted phenylimino-imidazolines. Eye trauma of the kind contemplated here can be by accident, by invasive surgery of any kind or non-invasive such as by laser. In fact the use of the present invention as adjunct to laser surgery or treatment is preferred. The advent of the laser as an ophthalmic surgical instrument has provided physicians with a means of performing non-invasive intraocular surgery, which offers many advantages over conventional invasive techniques previously utilized. While the advantages of performing non-invasive surgery are many, there are complications which arise as a result of the procedure. Among these is an acute postoperative intraocular pressure rise which occurs in 30–80% of eyes undergoing trabeculoplasty, iridotomy, and capsulotomy procedures using Q-switched Argon, Neodymium: YAG or Ruby Lasers. This complication has also been recognized to occur following conventional invasive cataract surgery, occurring following both intra- and extracapsular surgical techniques with or without intraocular lens implantation.

Various studies have shown that hypotensive drugs such as beta-adrenergic blockers, miotics, steroidal and non-steroidal antiinflammatory agents, and carbonic anhydrase inhibitors do not prevent the acute postoperative intraocular pressure increase following the previously mentioned ophthalmic surgical procedures. A need exists, therefore, for an ophthalmic hypotensive agent which is capable of preventing an acute rise and/or decreasing intraocular pressure following both invasive and non-invasive ophthalmic surgery.

Although the foregoing discussion relates to the need for a hypotensive agent in ophthalmic surgical procedures, it is readily apparent that such agents would also be useful in many other ophthalmic conditions involving a requirement to decrease intraocular pressure.

SUMMARY OF THE INVENTION

A principal object of the present invention is the provision of a method for reducing intraocular pressure during and after ophthalmic invasive or non-invasive surgical procedures, or other eye trauma.

The foregoing objects as well as other general objects of the present invention are achieved by providing a method of reducing intraocular pressure which comprises topically applying a composition containing a clonidine derivative to the affected eye.

DETAILED DESCRIPTION OF THE INVENTION

The present invention utilizes certain clonidine derivatives, as defined above, to control intraocular pressure of the eye during invasive or non-invasive ophthalmic surgery. Clonidine is a known hypotensive compound, and is described, for example, in U.S. Pat. No. 3,202,660; the contents of this patent relating to the structure, preparation and physical properties of this compound are incorporated herein by reference.

It has previously been discovered that certain derivatives of this compound are effective in lowering intraocular pressure when applied topically to the eye. This discovery is described in U.S. Pat. No. 4,461,904, the entire contents of which are incorporated herein by reference. The clonidine derivatives described in this patent are 2-(trisubstituted phenylamino)-imidazoline compounds, which are also known as 2-(trisubstituted anilino)-1,3-diazacyclopentene-(2) compounds. Reference is made to this patent for further details concerning the structure, preparation and physical properties of these clonidine derivatives. Related developments in connection with the above-cited discovery are described in U.S. Pat. Nos. 4,517,199; 4,587,257; and 4,515,800; and in commonly assigned application Ser. No. 590,464, filed Mar. 16, 1984. The foregoing documents are incorporated herein by reference to the extent that they disclose the subject clonidine-like compounds generically and specifically.

A preferred group of 2-(trisubstituted phenylimino)imidazoline compounds having the above-described hemostatic utility are those of formula:

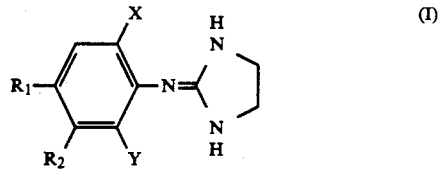

wherein: $R_1$ and $R_2$ are selected from H, OH, NHR and

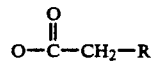

with R' being selected from H and $C_1$-$C_4$ alkyl, provided that one of $R_1$ and $R_2$ is hydrogen; and X and Y are selected from Br, Cl, $CH_3$ and $CH_2CH_3$. Specific examples of Compounds from this group are set forth in Table 1 below:

TABLE 1

| Compound | R₁ | R₂ | X | Y |
|---|---|---|---|---|
| 1 | NHCH₃ | H | CH₃ | CH₃ |
| 2 | NHCH₃ | H | CH₂CH₃ | CH₂CH₃ |
| 3 | NHCH₃ | H | Cl | Cl |
| 4 | NH₂ | H | Br | Br |

A group of especially preferred clonidine derivatives of formula (I) are those in which $R_1$ and $R_2$ are selected from H and $NH_2$, provided that one of $R_1$ and $R_2$ is H, and X and Y are selected from Cl, $CH_3$, and $CH_2CH_3$. Specific examples of compounds from this group are set forth in Table 2 below:

TABLE 2

| Compound | R₁ | R₂ | X | Y |
|---|---|---|---|---|
| 5 | H | NH₂ | CH₃ | CH₃ |
| 6 | NH₂ | H | CH₂CH₃ | CH₂CH₃ |
| 7 | H | NH₂ | Cl | Cl |
| 8 | NH₂ | H | CH₂CH₃ | Cl |
| 9 | NH₂ | H | CH₃ | Cl |
| 10 | NH₂ | H | CH₂CH₃ | CH₃ |
| 11 | NH₂ | H | CH₃ | CH₃ |
| 12 | H | NH₂ | CH₂CH₃ | CH₂CH₃ |
| 13 | NH₂ | H | Cl | Cl |

Of these specific examples, p-aminoclonidine (i.e., compound 13) has been found to be particularly well-suited for use in the present invention.

Another preferred group of clonidine derivatives having the above-described hemostatic utility are those of formula:

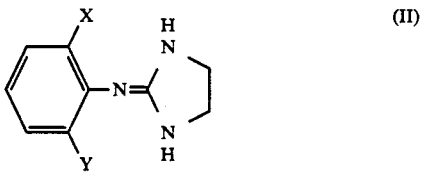

wherein: X and Y are selected from Br, Cl, $CH_3$ and $CH_2CH_3$, with the provision that at least one of X and Y is alkyl. Compounds of this type are described, for example, in U.S. Pat. No. 3,468,887, and *J. Med. Chem.*, Vol. 19, pages 1049-54 (1976); the contents of these publications relating to the structure, preparation and physical properties of these compounds are incorporated herein by reference. Specific examples of compounds from this group are set forth in Table 3 below.

TABLE 3

| Compound | X | Y |
|---|---|---|
| 14 | CH₂CH₃ | CH₂CH₃ |
| 15 | CH₂CH₃ | CH₃ |
| 16 | Cl | CH₂CH₃ |

There are no other preferences respecting the clonidine derivatives which may be utilized in this invention so long as the derivatives selected are capable of lowering IOP of the eye without causing mydriasis when topically applied to the eye at the clinical concentrations described below.

The above-described compounds may be effectively utilized as ocular hypotensive agents when applied topically to the eye in a concentration of from about 0.05% to 5% by weight. The compounds may be incorporated into various types of ophthalmic formulations according to known techniques. Ophthalmic solutions and suspensions are the preferred dosage forms. Typically such dosage forms are adjusted to isotonicity with sodium chloride, Thickening agents such as carboxymethylcellulose, or carbopol may also be employed to enhance delivery. The pH of such dosage forms is typically adjusted to be within the range of 6.0 to 8.0 with HCl or NaOH.

It is contemplated that the compounds will normally be applied preoperatively in order to provide decreased intraocular pressure over a relatively short period (i.e., 1-24 hours) prior to the surgical procedure. The compounds should also be applied, for example, in a series of multiple doses following surgery in order to control postsurgical intraocular pressure for a period of approximately 7 days. It is contemplated that a number of different uses of the above-described compounds for control of intraocular pressure will be developed, for example, for control of intraocular pressure following trauma. Accordingly, the present specification should not be interpreted as limiting the inventive use of these compounds to only surgically related procedures.

The invention has been described herein with reference to certain preferred embodiments. However, as obvious variations thereon will become apparent to those skilled in the art, the invention is not to be considered as limited thereto.

What is claimed is:

1. A method of controlling or preventing an acute post-operative intraocular pressure rise associated with an ophthalmic laser surgical procedure, which comprises topically applying to the involved eye prior and subsequent to the procedure an amount of an imidazoline compound effective to control such an acute post-operative intraocular pressure rise, said imidazoline compound having the formula:

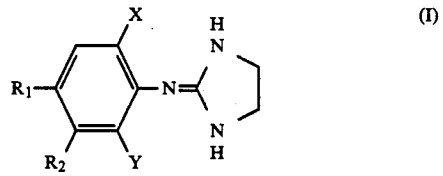

wherein: $R_1$ and $R_2$ are selected from the group consisting of H, OH, and NHR', wherein R' is selected from the group consisting of H and $C_1$-$C_4$ alkyl, provided that one of $R_1$ and $R_2$ is always hydrogen; and X and Y are selected from the group consisting of Br, Cl, $CH_3$ and $CH_2CH_3$, or a pharmaceutically acceptable free base or acid salt thereof.

2. The method of claim 1 wherein $R_1$ is $NHCH_3$, $R_2$ is H, X is $CH_3$ and Y is $CH_3$.

3. The method of claim 1 wherein $R_1$ is $NHCH_3$, $R_2$ is H, X is $CH_2CH_3$ and Y is $CH_2CH_3$.

4. The method of claim 1 wherein $R_1$ is $NH_2CH_3$, $R_2$ is H, X is Cl and Y is Cl.

5. The method of claim 1 wherein $R_1$ is $NH_2$, $R_2$ is H, X is Br and Y is Br.

6. The method of claim 1 wherein $R_1$ and $R_2$ are selected from H and $NH_2$ and X and Y are selected from Cl, $CH_3$ and $CH_2CH_3$.

7. The method of claim 6 wherein $R_1$ is H, $R_2$ is $NH_2$, X is $CH_3$ and Y is $CH_3$.

8. The method of claim 6 wherein $R_1$ is $NH_2$, $R_2$ is H, X is $CH_2CH_3$ and Y is $CH_2CH_3$.

9. The method of claim 6 wherein $R_1$ is H, $R_2$ is NH$_2$, X is Cl and Y is Cl.

10. The method of claim 6 wherein $R_1$ is NH$_2$, $R_2$ is H, X is CH$_2$CH$_3$ and Y is Cl.

11. The method of claim 6 wherein $R_1$ is NH$_2$, $R_2$ is H, X is CH$_3$ and Y is Cl.

12. The method of claim 6 wherein $R_1$ is NH$_2$, $R_2$ is H, X is CH$_2$CH$_3$ and Y is CH$_3$.

13. The method of claim 6 wherein $R_1$ is NH$_2$, $R_2$ is H, X is CH$_3$ and Y is CH$_3$.

14. The method of claim 6 wherein $R_1$ is H, $R_2$ is NH$_2$, X is CH$_2$CH$_3$ and Y is CH$_2$CH$_3$.

15. The method of claim 6 wherein $R_1$ is NH$_2$, $R_2$ is H, X is Cl and Y is Cl.

16. The method of claim 1 wherein the 2-(trisubstituted phenylimino)-imidazoline compound is applied to the eye in a concentration of from about 0.05% to 5% by weight.

17. A method of controlling or preventing an acute post-operative intraocular pressure rise associated with an ophthalmic laser surgical procedure, which comprises topically applying to the involved eye prior and subsequent to the procedure an amount of an imidazoline compound effective to control such an acute post-operative intraocular pressure rise, said imidazoline compound having the formula:

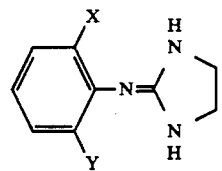

(II)

wherein: X and Y are selected from the group consisting of Br, Cl, CH$_3$ and CH$_2$CH$_3$, with the provision that at least one of X and Y is alkyl, or a pharmaceutically acceptable free base salt thereof.

18. The method of claim 17 wherein both X and Y are CH$_2$CH$_3$.

19. The method of claim 17 wherein X is CH$_2$CH$_3$ and Y is CH$_3$.

20. The method of claim 17 wherein X is Cl and Y is CH$_2$CH$_3$.

21. The method of claim 17 wherein the compound of formula (II) is applied to the eye in a concentration of from about 0.05% to 5% by weight.

22. A method of controlling or preventing an acute post-operative intraocular pressure rise associated with an ophthalmic laser surgical procedure which comprises topically applying to the involved eye prior and subsequent to the procedure an amount of a substituted phenylimino-imidazoline effective to control such an acute post-operative intraocular pressure rise.

* * * * *